United States Patent
Singh et al.

(10) Patent No.: US 9,228,980 B2
(45) Date of Patent: Jan. 5, 2016

(54) NON-DESTRUCTIVE EVALUATION METHODS FOR AEROSPACE COMPONENTS

(75) Inventors: Surendra Singh, Chandler, AZ (US); Robert Hogan, Chandler, AZ (US); Andy Kinney, Chandler, AZ (US); Jim Ohm, Tempe, AZ (US); Mark C. Morris, Phoenix, AZ (US); Donald G. Godfrey, Phoenix, AZ (US); Gregory Weaver, Rio Rancho, NM (US)

(73) Assignees: HONEYWLL INTERNATIONAL INC., Morris Plains, NJ (US); VIBRANT CORPORATION, Albuquerque, NM (US)

( * ) Notice: Subject to any disclaimer, the term of this patent is extended or adjusted under 35 U.S.C. 154(b) by 587 days.

(21) Appl. No.: 13/598,046

(22) Filed: Aug. 29, 2012

(65) Prior Publication Data

US 2014/0060188 A1    Mar. 6, 2014

(51) Int. Cl.
*G01N 29/12* (2006.01)
*G01N 29/44* (2006.01)

(52) U.S. Cl.
CPC ............ *G01N 29/12* (2013.01); *G01N 29/4436* (2013.01); *G01N 2291/014* (2013.01); *G01N 2291/02491* (2013.01); *G01N 2291/2694* (2013.01)

(58) Field of Classification Search
CPC ..... G01N 29/04; G01N 29/041; G01N 29/12; G01N 29/46; G01N 2291/014; G01N 2291/0231; G01N 2291/0421; G01N 2291/0422; G01H 13/00
USPC ........................................... 73/579, 602, 583
See application file for complete search history.

(56) References Cited

U.S. PATENT DOCUMENTS

| | | | |
|---|---|---|---|
| 5,065,630 | A | 11/1991 | Hadcock et al. |
| 5,293,555 | A | 3/1994 | Anthony |
| 5,448,125 | A | 9/1995 | Chu |
| 6,006,163 | A | 12/1999 | Lichtenwalner et al. |
| 6,192,759 | B1 | 2/2001 | Schoess |
| 7,075,424 | B1 | 7/2006 | Sundaresan et al. |
| 7,377,179 | B2 | 5/2008 | Anderson |
| 2007/0034009 | A1 | 2/2007 | Pado |
| 2009/0070048 | A1 | 3/2009 | Stothers et al. |
| 2011/0112775 | A1 | 5/2011 | Bramban |
| 2011/0219878 | A1 | 9/2011 | El-Bakry et al. |

OTHER PUBLICATIONS

Giurgiutiu, V. et al.; Damage Identification in Aging Aircraft Structures with Piezoelectric Wafer Active Sensors, Journal of Intelligent Material Systems and Structures, [http://jim.sagepub.com/content/15/9-10/673.short] Nov. 9, 2011.

(Continued)

*Primary Examiner* — Laura Martin
*Assistant Examiner* — Rose M Miller
(74) *Attorney, Agent, or Firm* — Ingrassia Fisher & Lorenz

(57) ABSTRACT

The disclosed embodiments generally relate to non-destructive evaluation methods. In an embodiment, a method for non-destructive evaluation of a aerospace component includes positioning a first plurality of sensors in the region of interest, positioning a second plurality of sensors in the region of interest, inducing a vibration in the region of interest using the first plurality of sensors and receiving a resonance frequency spectra using the second plurality of sensors, and comparing the received resonance frequency spectra against a reference spectra to determine the presence of an anomaly in the region of interest.

7 Claims, 8 Drawing Sheets

(56) References Cited

OTHER PUBLICATIONS

Finlayson, R. D. et al.; Health Monitoring of Aerospace Structures with Acoustic Emission and Acousto-Ultrasonics, NDT in the Aerospace Industry, Published by Insight, vol. 43, No. 3, Mar. 2001.

Sinha, D. N.: "Acoustic resonance spectroscopy (ARS)", IEEE Potentials, IEEE, New York, NY, vol. 11, No. 2, Apr. 1, 1992, pp. 10-13.

EP Search Report for Application No. 13 180 471.8 dated Nov. 26, 2013.

EP Communication for Application No. 13 180 471.8-1554 dated Sep. 12, 2013.

NON-DESTRUCTIVE EVALUATION METHODS FOR AEROSPACE COMPONENTS

TECHNICAL FIELD

The disclosed embodiments generally relate to non-destructive evaluation (NDE) methods. More particularly, the disclosed embodiments relate to NDE methods for the evaluation of aerospace components.

BACKGROUND

Non-Destructive Evaluation (NDE) methods refer to a class of methods that can be used to inspect objects for defects. NDE methods are often used to inspect materials for defects, such as structural anomalies, inclusions, cracks, etc. However, many conventional NDE methods often provide incomplete or otherwise inadequate inspections. This is especially true in aerospace components, where manufacturing integrity and lifecycle monitoring are critical to the safe and effective operation of such components.

It would therefore be desirable to provide NDE methods for use with aerospace components that may be used to monitor manufacturing processes and to monitor the components during their lifecycle. Furthermore, other desirable features and characteristics of the present invention will become apparent from the subsequent detailed description of the invention and the appended claims, taken in conjunction with the accompanying drawings and this background of the invention.

BRIEF SUMMARY

The disclosed embodiments relate to non-destructive evaluation (NDE) methods for evaluating an aerospace component. In one embodiment, a method for non-destructive evaluation of an aerospace component includes identifying a region of interest on the aerospace component, positioning a plurality of sensors in the region of interest, inducing a vibration in the region of interest using the plurality of sensors and receiving a resonance frequency spectra using the plurality of sensors, and comparing the received resonance frequency spectra against a reference spectra to determine the presence of an anomaly in the region of interest.

In another embodiment, a method for non-destructive evaluation of an aerospace component includes inducing a vibration in a region of interest using a plurality of sensors and receiving a resonance frequency spectra using the plurality of sensors and comparing the received resonance frequency spectra against a reference spectra to determine the presence of an anomaly in the region of interest.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

The present invention will hereinafter be described in conjunction with the following drawing figures, wherein like numerals denote like elements, and wherein.

DETAILED DESCRIPTION

Figure 1:
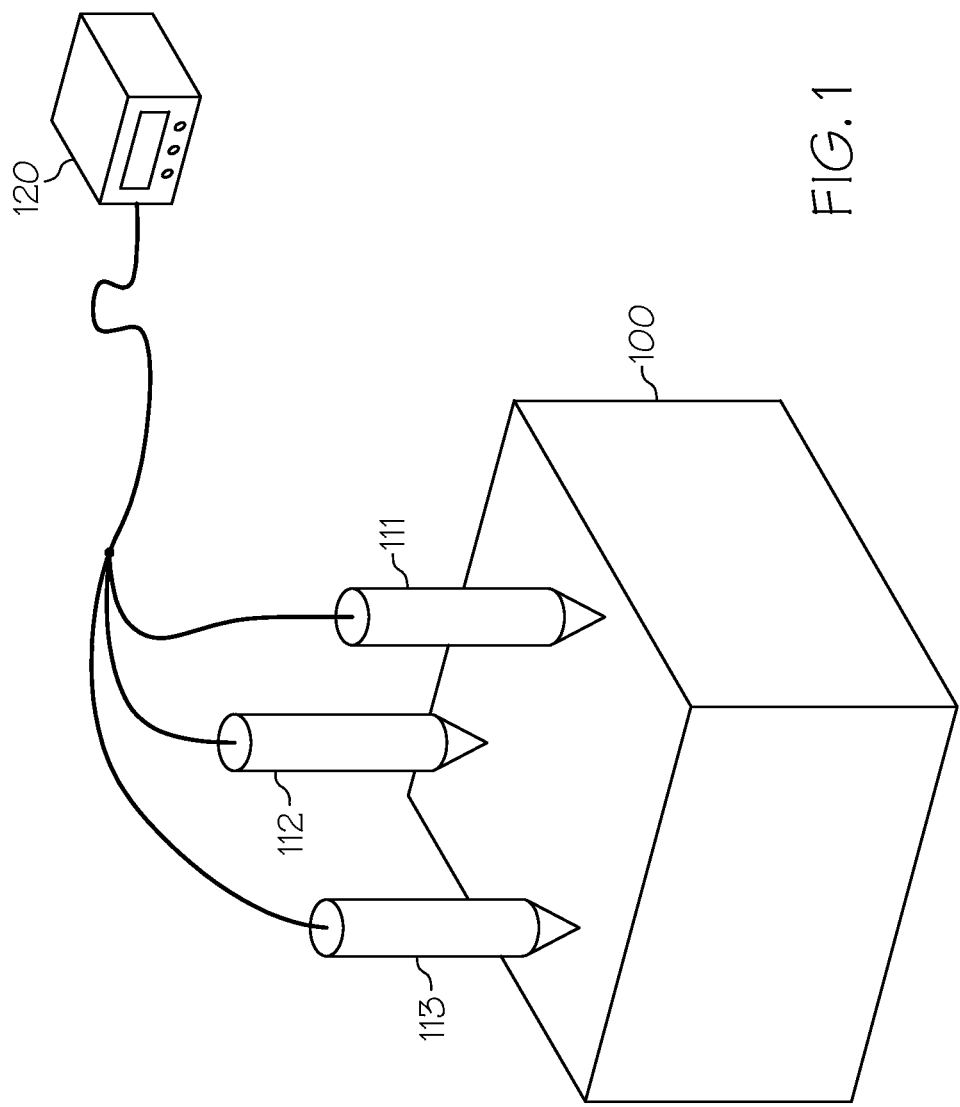
FIG. 1 illustrates a conceptual testing acoustic sensor arrangement on a region of interest in accordance with an embodiment of the present disclosure.

The following detailed description is merely exemplary in nature and is not intended to limit the invention or the application and uses of the invention. As used herein, the word "exemplary" means "serving as an example, instance, or illustration." Any embodiment described herein as "exemplary" is not necessarily to be construed as preferred or advantageous over other embodiments. Furthermore, there is no intention to be bound by any theory presented in the preceding background or the following detailed description.

Overview of the Disclosed Embodiments

The disclosed embodiments generally relate to non-destructive evaluation (NDE) methods. More particularly, the disclosed embodiments relate to NDE methods for the evaluation of aerospace components. In a first aspect of the present disclosure, embodiments will be described that use NDE methods to monitor the manufacturing process of aerospace components. In particular, the described methods may be effectively employed to determine the presence of anomalies in such components, or to determine the existence of variation among manufactured lots of such components, for example from different suppliers or from different manufacturing machinery. In a second aspect of the present disclosure, embodiments will be described that use NDE methods to monitor aerospace components during their lifecycle. In particular, the described methods may be effective employed to determine the presence of cracks or other weaknesses that may develop in such components during the course of their use. The advantage attendant by the use of the novel methods described herein will become apparent based on the following description of each.

NDE Methods Employed in the Disclosed Embodiments

The embodiments described herein are based on the fundamental principle of physics that a hard element will resonate at a specific frequency. As such, it has been discovered that it is possible to use specialized sensors in various configurations and combinations with other sensing devices, for example an optical interferometer, as will be described in greater detail below, for studying various aerospace components. Further, it has been shown that the structural integrity of the aerospace components is preferably studied by examining it under vibratory loads. As such, the present disclosure describes a non-destructive test method to evaluate each specific area using induced vibration within the aerospace components and to provide information related to local as well as bulk changes in microstructure and structural integrity.

Embodiments of the present disclosure are further based on the principle that an aerospace components with, for example, tight joints, nominal dimensions, acceptable microstructure, and elastic properties will show a markedly different response to induced vibration than aerospace components with loose joints and different alloying and heat treatment in which internal damping and additional resonances are present. Lack of tight joints, widening dimensions between joined components, cracks or other defects in microstructure, and inelastic properties or brittleness are all indicative of an assembly that could be prone to failure. It is thus an object of the present disclosure to identify such assemblies using non-destructive evaluation techniques.

In accordance with the present disclosure, a plurality of acoustic sensors are brought into contact with the region of interest (ROI) on the aerospace components to be tested. A first of the plurality of acoustic sensors subjects the aerospace components to external sinusoidal waves varying in frequency by the frequency sending/receiving processor 120. At least two other acoustic sensors of the plurality of acoustic sensors receive different vibrational response modes as the signals pass through the aerospace components and are received by the at least two receiving sensors. FIG. 1 conceptually depicts this arrangement, using one driving acoustic sensor 111 to induce a vibration using sinusoidal waves into the region of interest, illustrated as object 100 (e.g., an exemplary aerospace component), and two receiving acoustic sensors 112, 113 to receive the vibrational response modes after passing through the object 100.

As such, the aerospace component 100 is subjected to mechanical vibrations at different frequencies via acoustic sensors that convert electric sinusoidal waves into mechanical waves. The modes and frequency of vibrations in a part depends on its geometry, mechanical rigidity, elastic properties, alloying, heat treatment, and microstructure as shown below in equation 1. Resonant frequencies are determined by dimensions and material properties of joined component, accordingly to the following widely-known formula: $f_r \sim SQRT(k/m)$ Equation 1; where $f_r$=resonant frequency; k=stiffness (elastic properties e.g., Young's Modulus); and m=mass (volumetric dimensions, density). Structural defect strength reduction may be caused by degraded material properties, changes in metallographic microstructure, or dimensional variation e.g., a crack reduces stiffness and lowers the resonant frequency, which can be observed on the output signal. Further, the driving frequency applied to the object depends on the mass and geometry of the object. In general, objects with relatively higher mass are driven with relatively lower frequencies than relatively lower mass objects.

Other waveforms are possible. For example, in an embodiment, inducing a vibration includes inducing a sinusoidal wave of vibration frequencies. In another embodiment, receiving a resonance frequency includes receiving surface acoustic waves. In yet another embodiment, receiving a resonance frequency includes receiving longitudinal waves. In a further embodiment, receiving a resonance frequency includes receiving shear waves.

In an embodiment, the plurality of acoustic sensors is deployed on a region of interest for non-destructive evaluation as a phased array of acoustic sensors. In one example, the phased array of acoustic sensors is used for both driving and receiving vibrations/frequencies. In another example, the phased array of acoustic sensors is used for driving the vibration in the region of interest and optical sensors, such as an optical interferometer, are used for receiving the resonance frequencies as they pass through the region of interest. The present disclosure should not be read as limited to any particular number of sensors in the phased array, nor limited to any particular wave mode resonance frequency with regard to the function of such acoustic sensors.

In an alternative embodiment, sensors can be provided as optical sensors. For example, the sensors can be provided as optical interferometers. Using optics, the sensors are similarly able to determine the resonance frequencies in the object (e.g., an aerospace component. The various modes of waves as noted about are receivable using optical sensors in the same manner as noted above.

As part of this testing, software algorithms are used to characterize the spectral differences, such as "Q", Bandwidth (BW), Peak frequency, center frequency, and 3 dB and 6 dB BW between known accepted parts and rejected components. These differences are used to "train" the system to screen hardware based on these acceptable and unacceptable spectra. In this way, parts can be set up for automated inspection.

In principle, a variety of acoustic sensing technologies may be employed to detect defects in components, according to the methods and techniques described above. In one approach, as noted above, the use of acoustic sensors for both the driver and receiver units may be employed. In another approach, the use of acoustic sensors for the driver, and optical sensors for the receivers is employed. In a further approach ultrasonic sensors may be employed, as will be discussed in greater detail below. In yet another fourth approach, non-linear acoustics may be employed, as will be discussed in greater detail below. Regardless of the approach employed, the method of FIG. 2 (as will be discussed in greater detail below) illustrates the techniques necessary to perform NDE.

Regarding the use of ultrasonic sensors, embodiments of the present disclosure may employ either or both of conventional ultrasonics and phased array ultrasonics. As is known in the art, conventional ultrasonic transducers for NDE commonly include either a single active element that both generates and receives high frequency sound waves, or two paired elements, one for transmitting and one for receiving (T/R). In alternative embodiments, phased array probes, on the other hand, typically consist of a transducer assembly with from 16 to as many as 256 small individual elements that can each be pulsed separately. These may be arranged in a strip (linear array), a ring (annular array), a circular matrix (circular array), or a more complex shape.

Transducer frequencies are most commonly in the range from 2 MHz to 20 MHz. A phased array system will also include a computer-based instrument that is capable of driving the multi-element probe, receiving and digitizing the returning echoes, and plotting that echo information in various standard formats. A phased array system utilizes the wave physics principle of phasing, varying the time between a series of outgoing ultrasonic pulses in such a way that the individual wave fronts generated by each element in the array combine with each other to add or cancel energy in predictable ways that effectively steer and shape the sound beam. This is accomplished by pulsing the individual probe elements at slightly different times. Frequently the elements will be pulsed in groups of 4 to 32 in order to improve effective sensitivity by increasing aperture, which reduces unwanted beam spreading and enables sharper focusing.

Software known as a focal law calculator establishes specific delay times for firing each group of elements in order to generate the desired beam shape, taking into account probe and wedge characteristics as well as the geometry and acoustical properties of the test material. The programmed pulsing sequence selected by the instrument's operating software then launches a number of individual wave fronts in the test material. These wave fronts in turn combine constructively and destructively into a single primary wave front that travels through the test material and reflects off cracks, porosity, discontinuities, back walls, and other material boundaries like any conventional ultrasonic wave. The beam can be dynamically steered through various angles, focal distances, and focal spot sizes in such a way that a single probe assembly is capable of examining the test material across a range of different perspectives. This beam steering happens very quickly, so that a scan from multiple angles or with multiple focal depths can be performed in a small fraction of a second.

The returning echoes are received by the various elements or groups of elements and time-shifted as necessary to compensate for varying wedge delays and then summed. For example, a "C-Scan" is a two dimensional presentation of data displayed as a top or planar view of a test piece, similar in its graphic perspective to an x-ray image, where color represents the gated signal amplitude at each point in the test piece mapped to its x-y position. With conventional instruments, the single-element transducer must be moved in an x-y raster scan pattern over the test piece. With phased array systems, the probe is typically moved physically along one axis while the beam electronically scans along the other. Encoders will normally be used whenever precise geometrical correspondence of the scan image to the part must be maintained, although un-encoded manual scans can also provide useful information in many cases.

As noted above in accordance with yet a further alternate embodiment, non-linear acoustics may be employed in any of the testing schemes described herein (in addition to the standard acoustics and ultrasonics noted above). In this embodiment, scanning the region of interest may be accomplished using a non-linear ultrasonic driver and using several receivers for receiving several multiple harmonics for analyzing structural integrity, and producing a scan image thereby. For non-linear acoustics, additional frequencies are generated by any external discontinuities present in the structure. The NDE approach disclosed herein is based on ASTM E2534 as well as known literature on non-linear acoustics. In an exemplary implementation thereof, a tone burst narrow band is used for vibration and a wideband receiver is used for recording output.

Figure 2:
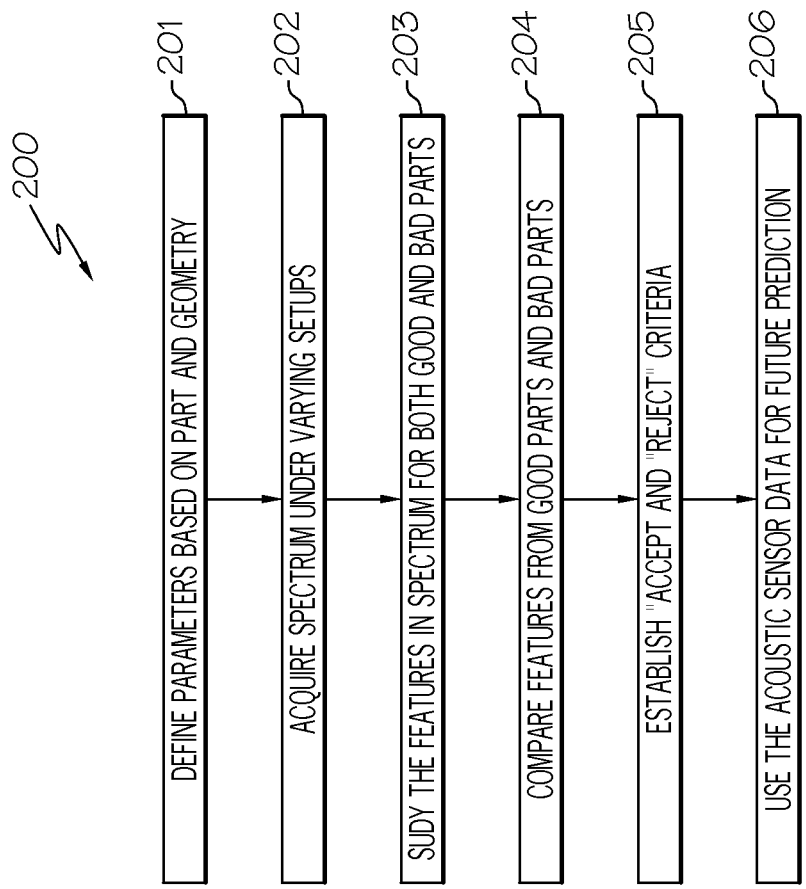
FIG. 2 is a flowchart of an exemplary method for non-destructive evaluation (NDE) of aerospace components in accordance with the present disclosure.

With regard to any of the above-discussed NDE approaches, an exemplary method 200 for non-destructive evaluation of aerospace components is illustrated as a flowchart in FIG. 2. The method 200 begins with a step of defining parameters based on part type and geometry. As will be appreciated, aerospace components are manufactured in many different shapes and sizes. As such, the method includes a step of defining parameters step 201 such as the region of interest, number of acoustic, ultrasonic, or optical sensors to be used, and types of wave forms (modes) to evaluate.

The exemplary method 200 continues with respect to step 202. At step 202, spectra are acquired under the varying setups or parameters defined in step 201. In order to acquire a sufficient sample size of spectra, a plurality of both acceptable aerospace components (i.e., aerospace components with no known defects or anomalies) and unacceptable aerospace components (i.e., aerospace components with known defects or anomalies) are provided. Each of these aerospace components is then tested using each of the setups defined by the previous determined parameters. The result is a number of resonance spectra that can be subjected to further analysis.

As such, the exemplary method 200 continues at step 203 with studying the features in the acquired spectra for both acceptable and unacceptable aerospace components. Here, the differences will be noted between parts that are known to be acceptable and parts that are known to be unacceptable. Differences between the spectra of any given part will become apparent to the skilled artisan upon visual or computerized inspection. This comparison, step 204 of method 200, is preferably performed using computerized inspection for both cost and accuracy considerations. Various software programs known in the art may be employed to analyze the spectra, make comparisons, and determine the differences found between the spectra of acceptable parts and the spectra of unacceptable parts.

With reference now to step 205 of method 200, one or more criteria are established for making future determinations as to whether an aerospace components will be considered acceptable or unacceptable. The criteria are based on the observed difference in spectra between the known acceptable and unacceptable aerospace components. For example, one criterion may be established as the presence or absence of a certain defined peak on the spectra. If the peak is present, then the aerospace component passes this criterion. If the peak is not present, then the aerospace component does not pass this criterion, and is rejected.

Finally, with reference to step 206 of method 200, sensor testing spectral data can be continuously gathered as more aerospace components are tested in the course of performing the present method. The additional data provided can be used to update and refine the criteria, if needed. It is expected that the foregoing method will be suitable for use in connection with the particular NDE implementations as will be described in greater detail below. In particular, it is expected that the foregoing method will be useful during manufacturing quality inspections and comparisons, as well as during life cycle testing and monitoring.

NDE to Identify Manufacturing Variations and Defects

Manufacturing critical aerospace components, for example engine parts such as cooled turbine nozzles and blades requires short, reliable product development cycle. Often the products cycle end up being longer than originally planned. This is due in part to unexpected obstacles present in the manufacturing processes. The intrinsic manufacturing problems range from poor manufacturing process control (MPC) to cost-prohibitive, long lead-times for tooling. The problem associated with cost-prohibitive and time-consuming tooling can be mitigated using innovative, lean manufacturing practices such as direct laser metal sintering (DLMS) methods. This will result in reduced product cycle time.

However, problems associated with manufacturing process control can still adversely affect the product delivery on schedules. Several factors including environment, measurements, human, machines, materials, and methods influence the manufacturing processes that, in turn, result in aerospace components with structural anomalies, poor dimensional tolerance, and variations in metallographic microstructure. Therefore, the need exists for some means for monitoring manufacturing process control. Monitoring not only the quality of the product, but also that of the process, will not only avoid both materials waste and long delay, but it will improve product development cycle time, reduce cost, and enhance quality.

Among several NDE methods that have traditionally been used for monitoring MPC include Fluorescent Penetrant Inspection (FPI), Magnetic Testing (MT), Ultrasonic Testing (UT), Eddy current testing (ET), and XRay testing (RT). Each of these NDE methods has certain inherent advantages and disadvantages. For example, RT and UT are suited for both volumetric and subsurface inspections, and FPI, MT, and ET are mostly suited for subsurface and surface inspections in parts. New emerging NDE methods, including acoustic sensors, Flash Thermography, Thermoacoustic Imaging (TA1) and Laser Shearography offer excellent alternatives. In particular, acoustic sensors testing can be used for monitoring manufacturing process control (MPC), evaluating Structural Integrity Assessment (SIA), and inspecting quality in variety of aerospace components, such as DMLS turbine stators, turbine blades, and hybrid bearings.

Figure 3:
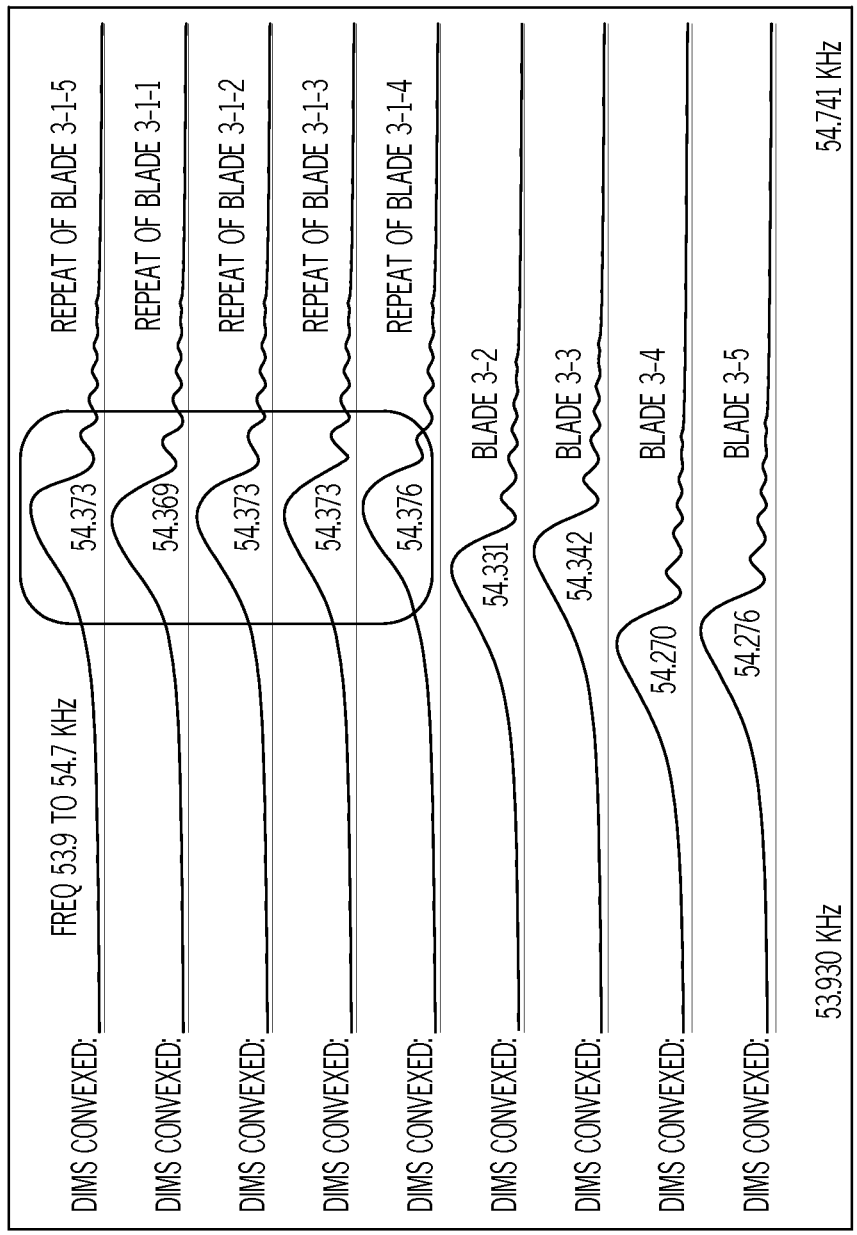
FIGS. 3 and 4 illustrate exemplary resonance spectra as may be acquired using the methods of the present disclosure.
Figure 4:
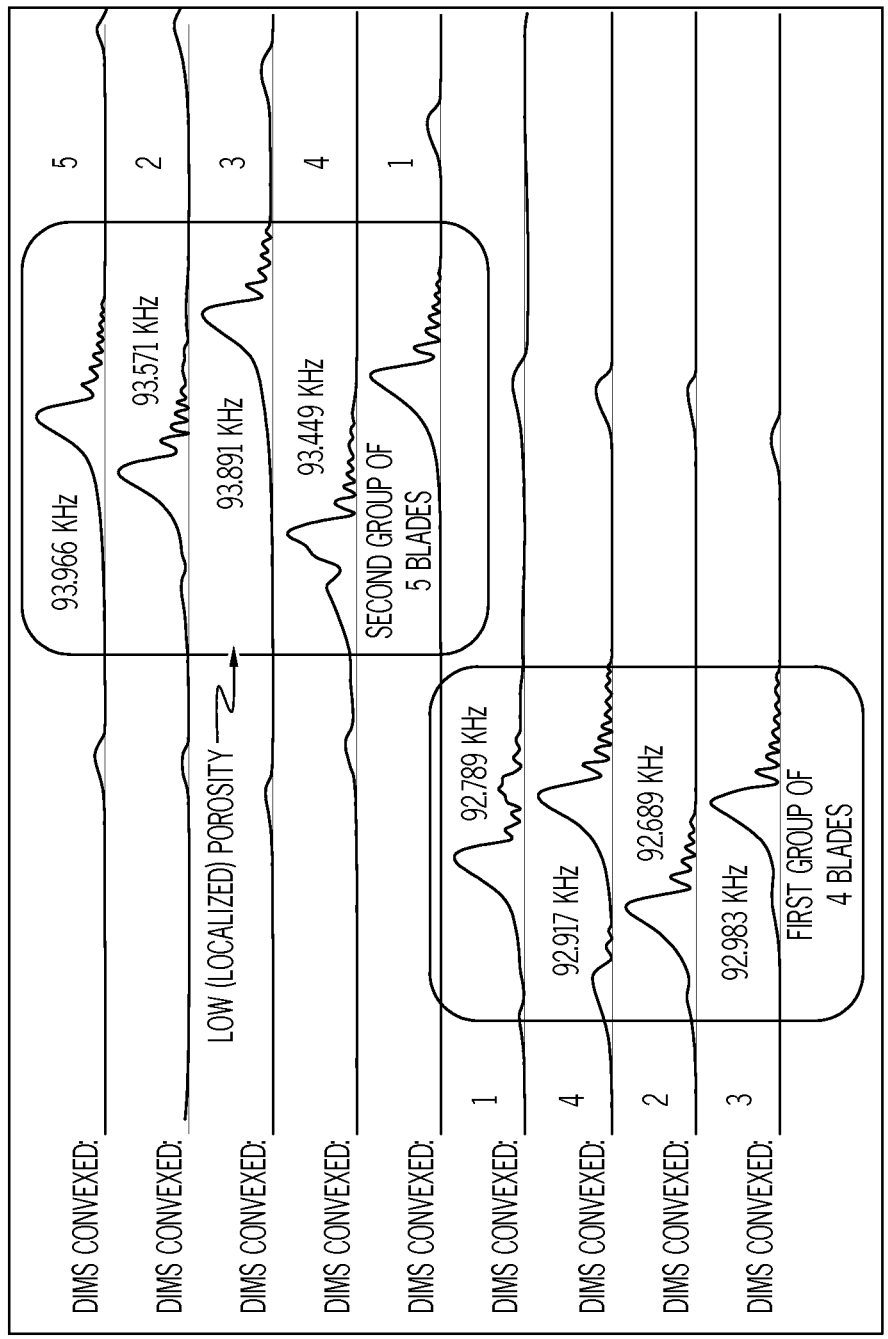

In an exemplary embodiment, representative acoustic sensor data (i.e., spectra) are depicted in FIGS. 3 and 4. The digital spectra data for DMLS blades show the presence of variations in a lot as well as variations between lots. The spectral difference between these two lots is known to be the result of a variation in porosity percentage between the lots. The lot #2 with five blades had lower porosity than the blades in Lot #1 (FIG. 4). It is therefore evident that DLMS blades built under similar manufacturing practices varied significantly, demonstrating the capability of acoustic sensor methods for monitoring manufacturing processes.

Embodiments of the present disclosure will facilitate revealing the existence of problems associated with manufacturing processes in the early stages of such manufacturing processes. For example, one can use acoustic sensors in early stage following the stress relieve cycle during an exemplary DMLS process flow for studying any changes in the structure in a part as a result of stress relief. Depending on the needs, acoustic sensors may also be used for studying the effect of different operations at various stages in DMLS component manufacturing processes.

Figure 5:
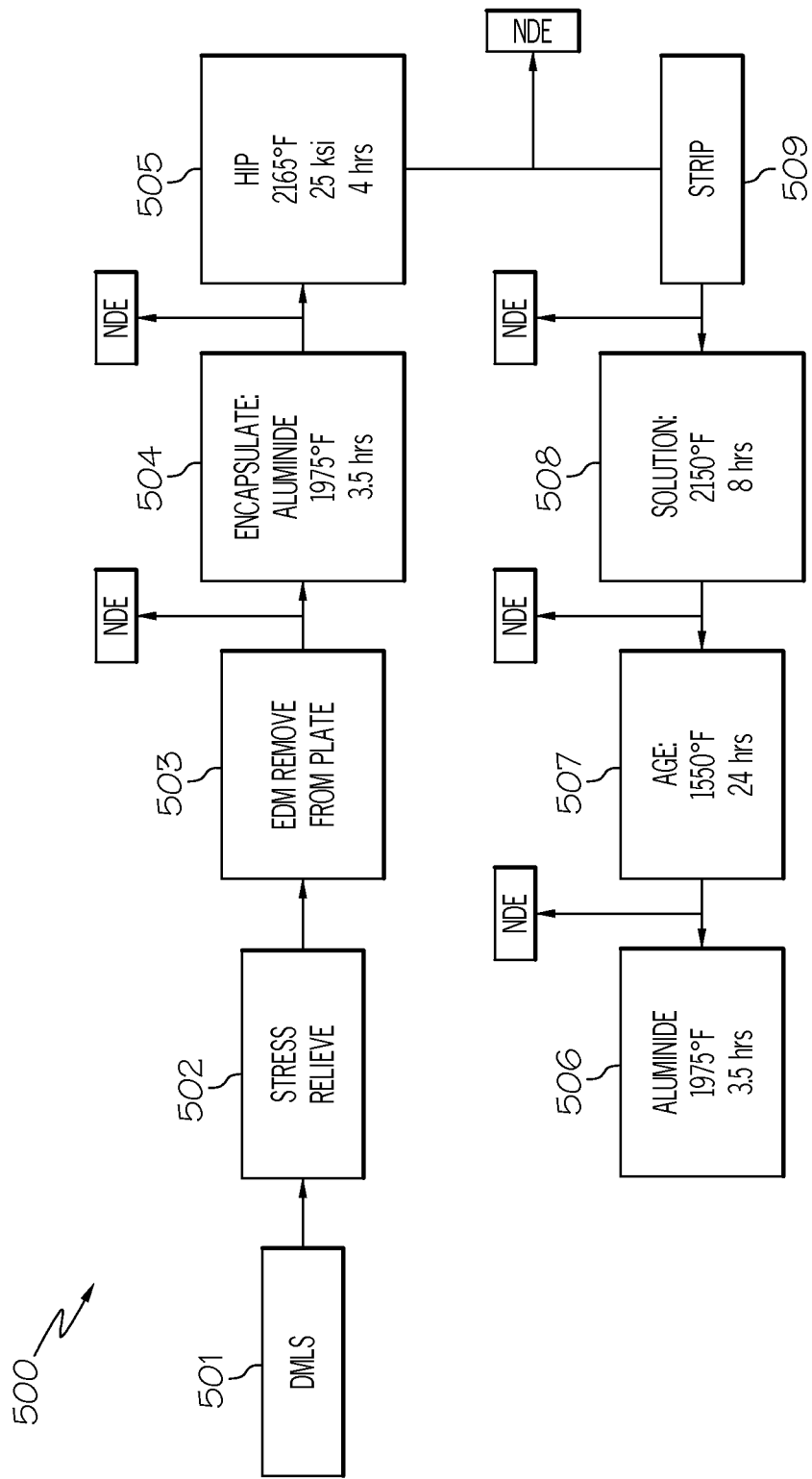
FIG. 5 is a flowchart of an exemplary NDE process.

FIG. 5 shows an exemplary process flow wherein acoustic sensors and other NDE methods can be used for DMLS blade manufacturing process monitoring. It should be appreciated that the depicted process flow is exemplary among many possible process flows, and is provided to give an indication of the versatility of using NDE methods during the manufacturing process to monitor process quality. As shown therein, NDE methods can be employed before or after nearly every phase (steps 503-509, inclusive) in the manufacturing process, once the aerospace component is initially formed.

Embodiments of the present disclosure deploy acoustic sensors at various stages that are critical in the manufacturing processes control. For example, in order to study whether the HIP processes has successfully eliminated porosity in a part, acoustic sensors may be used following HIP processes (FIG. 5). Similarly, acoustic sensors may also be employed following solutioning and aging processes to study the redistribution of Gamma and Gamma Prime in DMLS components fabricated with nickel base superalloy materials. In other embodiments, a similar approach may be applied for each stage deemed important for studying the structure-property relationship in the DMLS components.

Figure 6:
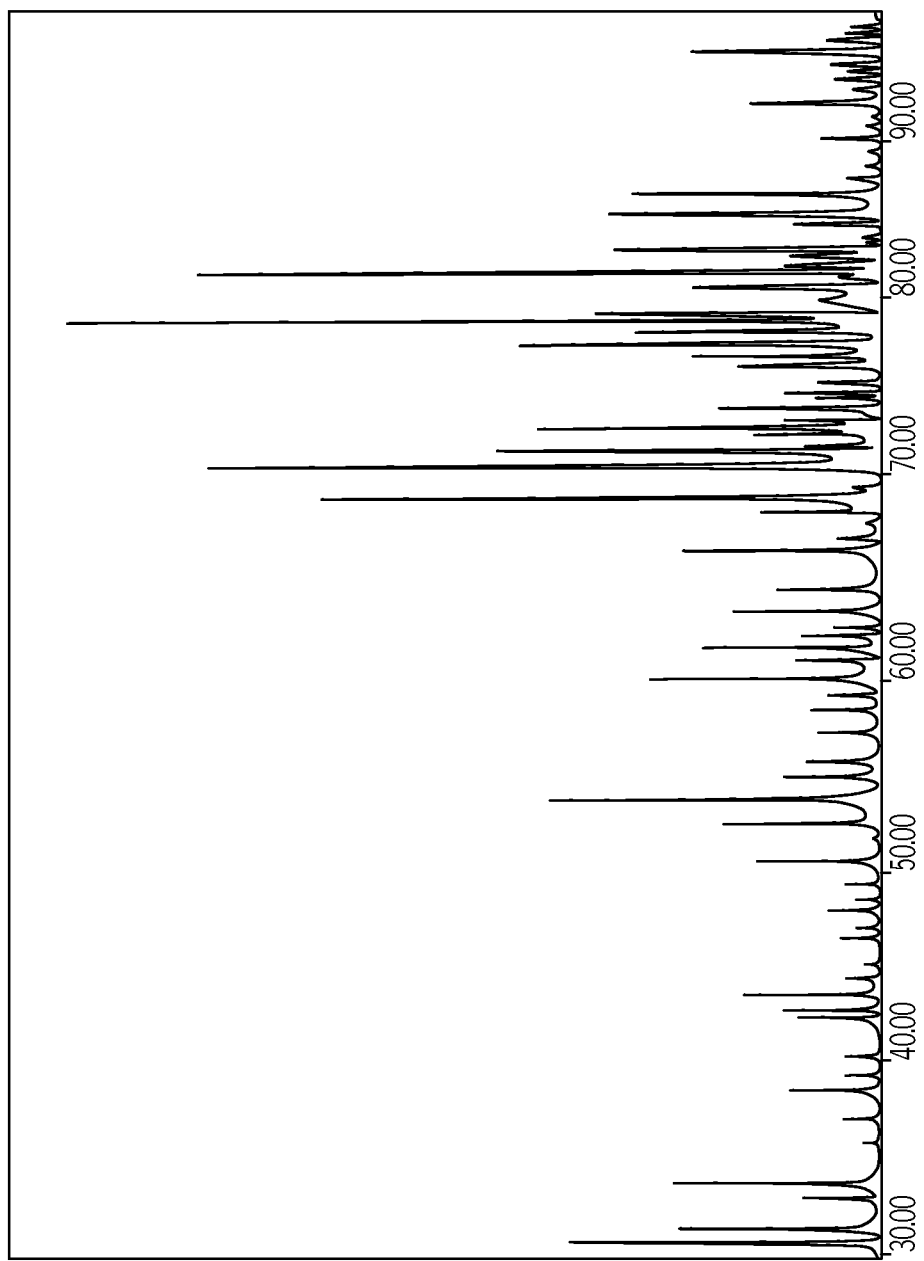
FIG. 6 is an exemplary resonance spectra as may be acquired performing the steps illustrated in FIG. 5.

The applications of acoustic sensors are fast, inexpensive, clean, and easy-to-use. The entire process takes normally less than a minute after the setup is fully validated, and it requires no chemical or any other environmental related issues. The normal process involves several steps: 1) Fixture for coupling the part to sensors, 2) decide the stage for deploying acoustic sensors, 3) defining frequency range of interests; 4) acquiring data, 5) analyzing the digital signatures, and 6) conclude and recommend. As such, reference is made in particular to the exemplary method outline above with regard to FIG. 2. In conjunction therewith, FIG. 6 shows a typical example of the acoustic sensors digital signatures for a DMLS turbine blade.

Unlike any other existing NDE methods, acoustic sensors possess several unique features that differentiate them from the existing NDE methods. For example, acoustic sensor results directly correlate to the structural integrity of the component. In comparison, current technologies highlight defects or indications of defects that could possibly affect the structural integrity of the component. Acoustic sensors require no interpretation by the operator and thus function as excellent screening tools. Prior art techniques require significant interpretation of test results by skilled personnel. Acoustic sensors do not require operator interpretation for the pass/fail determination, when employed in accordance with the methods described herein. Acoustic sensors test the entire component; it is a complete component evaluation. In comparison, most NDE technologies only test a specific portion of the component and can miss defects in un-inspected areas. Acoustic sensor testing takes only minutes with little or no part preparation and no hazardous waste. Current testing methods can require significant preparation and may require the use of chemicals or radiation. Furthermore, acoustic sensors have minimal waste stream.

In an exemplary testing implementation, the setup includes acoustic sensors, a computer for driving sensors, and receivers and computer for data analysis. As such, reference is made to FIG. 1, discussed above. The entire spectrum for an exemplary aerospace component is shown in FIG. 6. In order to fully evaluate a MPC or a component, there is need for NDE methods for continuous process monitoring. This can be achieved using acoustic sensors and thereby acquiring acoustic signatures at different stages at various stages as shown in FIG. 5. Using acoustic NDE methods, in an exemplary test, the difference between two lots is evident in the acoustic sensors data. With reference back to FIGS. 3 and 4, the data indicate that the acoustic sensor digital signatures have the capability to study the effect of porosity differences in components. As such, and by way of example, these NDE methods present a suitable means to study the effectiveness of HIP processes in manufacturing processes.

NDE to Monitor Life Cycle

The life span of an aerospace component is defined by three criteria/principles: 1) Retirement For Cause (RFC): these parts are not subjected to any scheduled inspection but are inspected during the engine tear down and have no upper limit until part is retired due to obvious defects. 2) Damaged Tolerance Design (DTL): this is based on the crack growth and is subject to scheduled inspections. And 3) Hard Life; this is typically based on Low Cycle Fatigue (LCF) and is retired after the hard life no matter whether the part appears acceptable or not.

Parts from the RFC and DTL categories are inspected at a defined interval, wherein each part is taken apart from the assembly followed by a set of NDE and other inspections. Most of these inspections have limited successes, as they are best suited only for detecting surface and subsurface anomalies and suffer from being subjective and time-consuming. In addition, these inspections often are not suited for volumetric inspections due to practicality involved. Consequently, parts belonging to the RFC and DTL groups are not 100% inspected during scheduled maintenance inspections.

Embodiments of the present disclosure employ an array of acoustic sensors, together with software and hardware, for studying local and global structural changes, including anomalies. The acoustic sensor based techniques described herein offer an innovative solution that is faster and cheaper than prior art methods and is environmentally friendly in nature. Embodiments of the described methods require no hazardous chemicals or radiation, and little to no part cleaning is necessary. They differ significantly from the existing NDE approaches and philosophy. The existing NDE methods emphasize more on the detection of cracks than the acoustic sensor method described herein. The latter is suited for monitoring any structural changes taking place as a whole. For example, existing NDE methods are unable to detect cumulative fatigue and damage preceding the onset of any catastrophic failure, whereas acoustic sensor methods have been discovered to demonstrate this capability.

Figure 7:
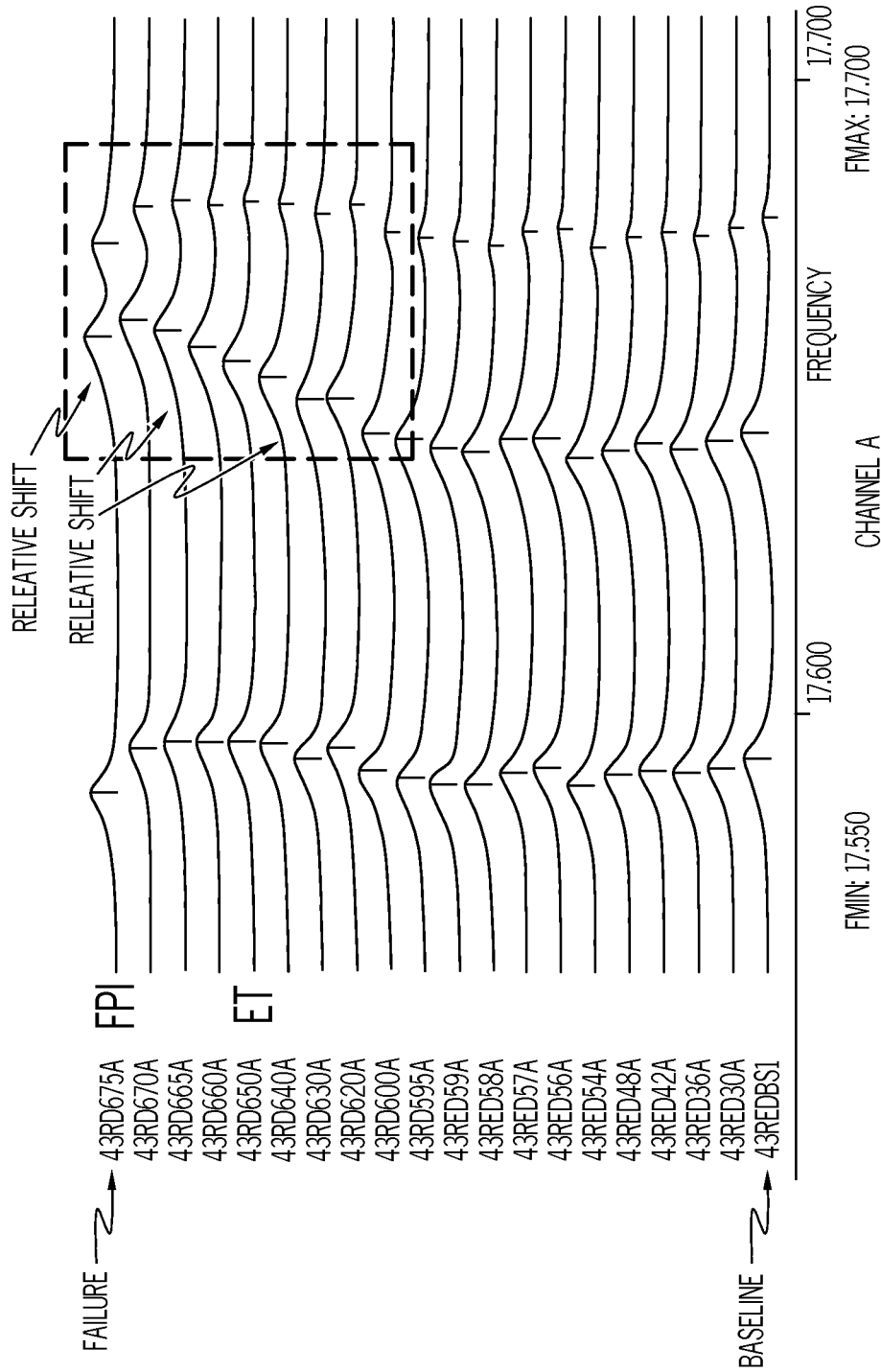
FIG. 7 illustrates a frequency shift as may be encountered using certain NDE techniques described herein.

For example, reference is now made to FIG. 7. FIG. 7 shows the changes in digital signatures in a cast wheel during a "Spin Pit" test. As shown therein, there is a relative shift in the digital signature as determined by acoustic sensor testing. This relative shift is indicative of cumulative fatigue occurring in the component.

Embodiments of the present disclosure employ an array of acoustic sensors, along with novel algorithms, and offer a unique approach for monitoring product structural integrity at various product development cycles in a component, from manufacturing to retirement. The disclosed method provides for a whole inspection of each component to study variation between components as a tool for monitoring Manufacturing Process Control (MPC) as well as "cradle-to-grave" inspection in a part to study changes in the part over its entire life. These inspection data can be stored in digital signature, providing a data base for different parts in a lot or for a part over a period of time.

In contrast to the existing NDE methods, wherein emphasis has been heavily placed to detect surface and subsurface anomalies, the disclosed acoustic sensor method will capture all changes in a part since the last inspection. These changes include microstructure (phase structure, grain size, hardness, and stiffness), density, initiation of new cracks and growth of the existing cracks, heat affected zones, and dimensional changes due to harsh operating environment. The methods assess changes in structural integrity preceding the onset of any fatigue and catastrophic failure well before that of any existing prior art NDE methods, and as noted above with regard to FIG. 7.

As noted, prior art NDE methods detect anomalies only after cracks have grown beyond a certain detectable size. Therefore, the presently described method offers several unique and novel features that are not present in prior art inspection methods. Further, the presently described method differs significantly from any other method known in the art in that it may employ an array of sensors optimally configured towards detecting both critical areas/region of interests (ROIs) and areas that are currently non-inspectable.

Figure 8:
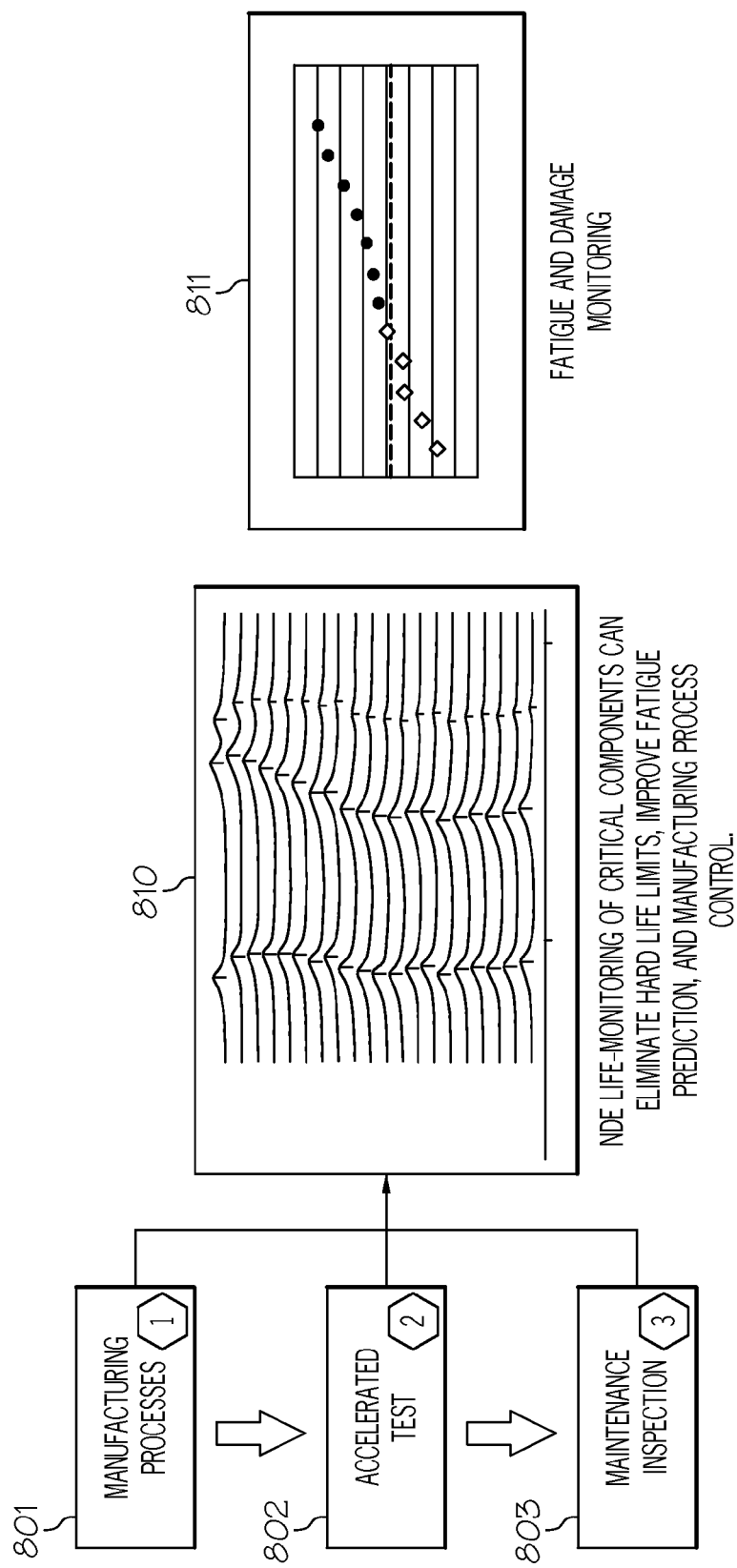
FIG. 8 is yet another exemplary flowchart of an NDE process.

The methods described herein can be used at various stages in the life cycle of an aerospace component, starting from manufacturing to inspecting quality to monitoring changes during maintenance, repair, and overall (MRO). As noted above in the previous section, in the early stage of manufacturing, these methods provide an excellent tool to study the manufacturing process control (MPC) wherein fingerprints via digital signatures from different parts will help for monitoring the MPC. The present invention replaces current sequential methods with a parallel approach, thereby eliminating any delay in providing feedback to the processes. For example, with reference to FIG. 8, the presently described methods are suitable for use in inspections during manufacturing (801), accelerated testing (802), and maintenance inspections (803). Each testing phase generates a digital signature, as noted in FIGS. 7 and 810 of FIG. 8. Thereafter, such data can be tracked over the lifetime of the component (811).

As such, disclosed herein are methods for non-destructive evaluation of aerospace components. Embodiments of the subject matter described herein allow for a wide range of applications in the areas of life assessment in an aerospace component, manufacturing process monitoring, and quality inspection and reliability. Manufacturing introduced anomalies can be quickly observed and unacceptable components rejected. Further, the sensors employed herein are capable of monitoring structural integrity between components fabricated under varying manufacturing conditions as well as returned from the field.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It is being understood that various changes may be made in the function and arrangement of elements described in an exemplary embodiment without departing from the scope of the invention as set forth in the appended claims.

What is claimed is:

1. A method for non-destructive evaluation of an aerospace component that is formed using direct metal laser sintering (DMLS), comprising:
   manufacturing the aerospace component using a DMLS manufacturing process, wherein manufacturing comprising at least forming the aerospace component and stress relieving the component, the manufacturing step including at least one of: aluminide encapsulating the component, hot-isostatic processing the component, ageing the component, or solutioning the component;
   prior to performing at least one of: aluminide encapsulating the component, hot-isostatic processing the component, ageing the component, or solutioning the component, identifying a region of interest on the manufactured aerospace component;
   positioning a plurality of acoustic sensors in the region of interest;
   inducing a vibration in the region of interest using the plurality of sensors and receiving a resonance frequency spectra using the plurality of sensors;
   comparing the received resonance frequency spectra against a reference spectra to determine the presence of an anomaly in the region of interest; and
   completing manufacturing the DMLS component by performing the at least one process step and any subsequent steps necessary to complete the manufacturing process.

2. The method of claim 1, wherein inducing a vibration comprises inducing a sinusoidal wave of vibration frequencies.

3. The method of claim 1, wherein receiving a resonance frequency comprises receiving surface acoustic waves.

4. The method of claim 1, wherein receiving a resonance frequency comprises receiving longitudinal waves.

5. The method of claim 1, wherein receiving a resonance frequency comprises receiving shear waves.

6. The method of claim 1, further comprising inducing a vibration in the region of interest of a reference aerospace component using the plurality of acoustic sensors and receiving a resonance frequency spectra using the plurality of acoustic sensors to produce the reference spectra.

7. The method of claim 1, wherein the method is employed as a life cycle monitoring NDE method.

\* \* \* \* \*